US00PP12040P2

(12) United States Plant Patent
Trees

(10) Patent No.: US PP12,040 P2
(45) Date of Patent: Aug. 7, 2001

(54) ANGELONIA PLANT NAMED 'BALANGDEUM'

(75) Inventor: Scott C. Trees, Nipomo, CA (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 09/476,002

(22) Filed: Dec. 31, 1999

(51) Int. Cl.[7] ..... A01H 5/00
(52) U.S. Cl. ..... Plt./263
(58) Field of Search ..... Plt./263

(56) References Cited

PUBLICATIONS

UPOV–ROM GTITM JOUVE Computer Database 2000/04, citations for 'Balangdeum', Aug. 2000.*

* cited by examiner

*Primary Examiner*—Bruce R. Campell
*Assistant Examiner*—W Couchoud Baker
(74) *Attorney, Agent, or Firm*—C. A. Whealy

(57) ABSTRACT

A new and distinct cultivar of Angelonia plant named 'Balangdeum', characterized by its dark purple-colored flowers; upright plant habit; freely basal-branching habit; and dark green leaves.

1 Drawing Sheet

BACKGROUND OF THE INVENTION

The present invention relates to a new and distinct cultivar of Angelonia plant, botanically known as *Angelonia augustifolia*, and hereinafter referred to by the cultivar name Balangdeum.

The new Angelonia is a product of a planned breeding program conducted by the Inventor in Arroyo Grande, Calif. The objective of the breeding program was to develop new compact Angelonia cultivars with unusual and attractive flower colors.

The new Angelonia originated from a cross made by the Inventor of the proprietary selection of *Angelonia augustifolia* identified as code number 545 as the male, or pollen parent, with the *Angelonia augustifolia* cultivar Blue Pacific, not patented, as the female, or seed parent. The cultivar Balangdeum was discovered and selected by the Inventor as a flowering plant within the progeny of the stated cross in a controlled environment in Arroyo Grande, Calif. in 1997. Plants of the new Angelonia and plants of its sibling cultivar, Balangpurp (U.S. Plant patent application Ser. No. 09/475,994), differ primarily in flower color.

Asexual reproduction of the new cultivar by terminal cuttings taken at Arroyo Grande, Calif., has shown the the unique features of this new Angelonia are stable and reproduced true to type in successive generations of asexual reproduction.

SUMMARY OF THE INVENTION

The following traits have been repeatedly observed and are determined to be the unique characteristics of 'Balangdeum'. These characteristics in combination distinguish 'Balangdeum' as a new and distinct cultivar:

1. Dark purple-colored flowers.
2. Upright plant habit.
3. Freely basal-branching habit.
4. Dark green leaves.

The new Angelonia differs primarily from the parent cultivar, code number 545, in flower color.

The new Angelonia can be compared to the parent cultivar, Blue Pacific. However, in side-by-side comparisons conducted by the Inventor in Arroyo Grande, Calif., plants of the new Angelonia differ from plants of the cultivar Blue Pacific in the following characteristics:

1. Plants of the new Angelonia are more compact, shorter and have shorter internodes than plants of the cultivar Blue Pacific.
2. Plants of the new Angelonia have larger leaves than plants of the cultivar Blue Pacific.
3. Plants of the new Angelonia and the cultivar Blue Pacific differ in flower color.

BRIEF DESCRIPTION OF THE PHOTOGRAPH

The accompanying photograph illustrates the overall appearance of the new cultivar as true as it is reasonably possible to obtain in colored reproductions of this type. Colors in the photographs may differ slightly from the color values cited in the detailed botanical description which more accurately describe the actual colors of the new Angelonia. The photograph comprises a side perspective view of a typical flowering plant of 'Balangdeum'.

DETAILED BOTANICAL DESCRIPTION

The cultivar Balangdeum has not been observed under all possible environmental conditions. The phenotype may vary somewhat with variations in environment such as temperature and light intensity, without, however, any variance in genotype. The following observations and measurements describe plants about 10 weeks after planting rooted cuttings and grown in 10-cm pots in West Chicago, Ill., under commercial practice in a double-layered acrylic-covered greenhouse with day temperatures about 21° C., night temperatures about 19° C., and light levels about 2,500 to 3,500 footcandles.

In the following description, color references are made to The Royal Horticultural Society Colour Chart except where general terms of ordinary dictionary significance are used.

Botanical classification: *Angelonia augustifolia* cultivar Balangdeum.

Parentage:

*Male parent.*—Proprietary selection of *Angelonia augustifolia* identified as code number 545, not patented.

*Female parent.*—*Angelonia augustifolia* cultivar Blue Pacific, not patented.

Propagation:

*Type cutting.*—Terminal cuttings.

*Time to initiate roots.*—About 7 days with 18° C.

*Time to develop roots.*—About 21 days with 18° C.

*Root description.*—Fibrous, fine, freely branching.

Plant description:

*Plant form.*—Upright.

*Growth and branching habit.*—Moderately vigorous. Freely basal-branching; pinching enhances branching. Appropriate for 10-cm containers.

*Crop time.*—About 7 to 10 weeks are required to produce a finished flowering plant from a rooted cutting.

*Plant height.*—About 21 cm.

*Lateral branches.*—Quantity per plant: About nine. Length: About 16.4 cm. Diameter: About 4.3 mm. Internode length: About 1 cm. Texture: Glandular, viscid. Color: Close to 144A.

*Foliage description.*—Leaves simple, symmetrical; abundant; opposite; sessile. Quantity of leaves per lateral branch: About 18. Length: About 6.2 cm. Width: About 1.8 cm. Shape: Linear to lanceolate. Apex: Acuminate. Base: Obtuse. Margin: Serrate. Texture: Puberulent. Color: Fully expanded leaves, upper surface: Close to 139A. Fully expanded leaves, lower surface: Close to 137C. Venation, upper surface: 145B. Venation, lower surface: 147B.

Flower description:

*Flower type, arrangement, habit.*—Freely and continuously flowering. Single two-lipped flowers arranged on terminal racemes. Usually about 17 flowers per raceme. Flowers self-cleaning. Slight sweet fragrance.

*Flowering season.*—Flowering is continuous from spring until fall.

*Flower size.*—Length: About 2.2 cm. Diameter: About 2.2 cm. Aspect: About 90° to flowering stem.

*Flower buds.*—Length: About 1 cm. Diameter: About 7 mm. Color: 137A.

*Petals.*—Quantity: Five, fused at base. Length: Upper petal, about 5 mm; lateral and lower petals, about 6 mm. Width: Upper petal, about 7 mm; lateral and lower petals, about 5 mm. Margin: Entire. Texture: Viscid. Color: Fully opened, upper surface: Between 83A and 86A. Fully opened, lower surface: 83B. Throat: 83C with splotches of 83A. Tube: Close to 79B.

*Calyx.*—Length: About 4 mm. Diameter: About 2 mm. Shape: Star-shaped. Color: 137A.

*Pedicels.*—Length: About 1.3 cm. Aspect: About 45° to flowering stem. Color: 144B with streaks of 183C.

*Reproducive organs.*—Androecium: Stamen number: Four. Stamen length: About 3 mm. Anther length: About 2 mm. Anther color: 102A. Amount of pollen: Moderate. Pollen color: 158D. Gynoecium: Pistil length: About 5 mm. Style color: Clear, colorless. Stigma color: Clear, colorless.

Disease resistance: Under commercial conditions, resistance and/or susceptibility to pathogens common to Angelonia has not been observed.

Drought tolerance: Plants of the new Angelonia have been observed to be relatively drought tolerant under outdoor conditions, as is typical of the species.

Seed development: Seed production has not be observed.

It is claimed:

1. A new and distinct cultivar of Angelonia plant named 'Balangdeum', as illustrated and described.

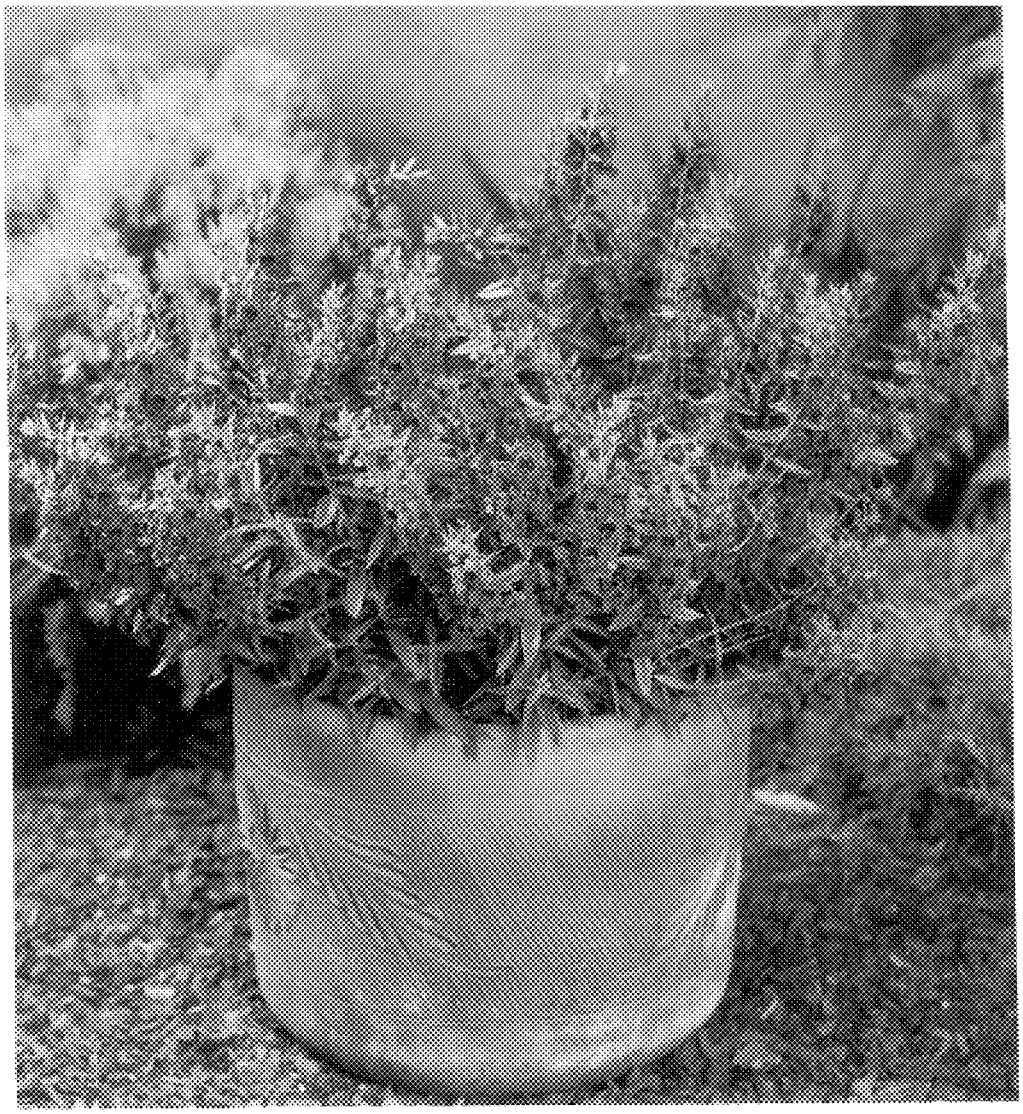

* * * * *